United States Patent
Rhein et al.

(10) Patent No.: US 10,264,991 B2
(45) Date of Patent: Apr. 23, 2019

(54) DEVICE FOR MEASURING PHYSIOLOGICAL VALUES

(71) Applicant: seca ag, Reinach (CH)

(72) Inventors: Detlef Rhein, Hamburg (DE); Till Garthoff, Hamburg (DE); Julian Brown, Bristal (GB)

(73) Assignee: SECA AG, Reinach (CH)

(*) Notice: Subject to any disclaimer, the term of this patent is extended or adjusted under 35 U.S.C. 154(b) by 0 days.

(21) Appl. No.: 15/034,621

(22) PCT Filed: Sep. 3, 2014

(86) PCT No.: PCT/IB2014/002093
§ 371 (c)(1),
(2) Date: May 5, 2016

(87) PCT Pub. No.: WO2015/044767
PCT Pub. Date: Apr. 2, 2015

(65) Prior Publication Data
US 2016/0278707 A1    Sep. 29, 2016

(30) Foreign Application Priority Data
Sep. 5, 2013  (DE) .................. 10 2013 014 982

(51) Int. Cl.
*A61B 5/0408*  (2006.01)
*A61B 5/00*    (2006.01)
*A61B 5/053*   (2006.01)

(52) U.S. Cl.
CPC ........ *A61B 5/04085* (2013.01); *A61B 5/0537* (2013.01); *A61B 5/683* (2013.01); *A61B 5/6829* (2013.01); *A61B 5/6832* (2013.01); *A61B 5/6838* (2013.01); *A61B 5/6892* (2013.01); *A61B 5/742* (2013.01); *A61B 2560/0214* (2013.01); *A61B 2562/22* (2013.01)

(58) Field of Classification Search
CPC .......................... A61B 5/04085; A61B 5/6892
USPC .......................................................... 600/393
See application file for complete search history.

(56) References Cited

U.S. PATENT DOCUMENTS

| 3,476,104 | A | * | 11/1969 | Davis | A61B 5/04085 |
| | | | | | 600/393 |
| 4,121,573 | A | * | 10/1978 | Crovella | A61B 5/0006 |
| | | | | | 128/903 |
| 5,224,479 | A | * | 7/1993 | Sekine | A61B 5/04085 |
| | | | | | 600/389 |
| 8,491,473 | B2 | * | 7/2013 | Wilson | A61B 5/00 |
| | | | | | 600/301 |

(Continued)

FOREIGN PATENT DOCUMENTS

DE    102010023122 A1    12/2011
EP         1627597 A1     2/2006

*Primary Examiner* — Lee S Cohen
(74) *Attorney, Agent, or Firm* — Lucas & Mercanti, LLP; Klaus P. Stoffel

(57) ABSTRACT

A device used to establish a contact between a subject and a measuring device using measurement technology, wherein the subject can be a patient. The device has at least one measuring device for connecting to the subject and at least one line to which the measuring device is secured. The line is designed such that the measured variables detected by the measuring device can be conducted to a measuring unit. A mat is connected to the at least one line so as to at least partly form an internal line section.

10 Claims, 3 Drawing Sheets

(56) References Cited

U.S. PATENT DOCUMENTS

| | | | |
|---|---|---|---|
| 9,332,919 B2* | 5/2016 | Crockford | A61B 5/0452 |
| 2003/0033675 A1* | 2/2003 | Solesbee | A61G 13/0018 |
| | | | 5/694 |
| 2007/0197925 A1* | 8/2007 | Moore | A61B 5/0408 |
| | | | 600/509 |
| 2010/0137704 A1 | 6/2010 | Vij et al. | |
| 2010/0324433 A1 | 12/2010 | Wilson et al. | |
| 2013/0072813 A1 | 3/2013 | Vogel | |
| 2017/0071500 A1* | 3/2017 | Von Maydell | A61B 5/7221 |

* cited by examiner

DEVICE FOR MEASURING PHYSIOLOGICAL VALUES

The present application is a 371 of International application PCT/IB2014/002093, filed Sep. 3, 2014, which claims priority of DE 10 2013 014 982,7, filed Sep. 5, 2013, the priority of these applications is hereby claimed and these applications are incorporated herein by reference.

BACKGROUND OF THE INVENTION

The invention pertains to a device for establishing contact between a subject and a measuring unit using measurement technology, comprising at least one measuring means for connecting to the subject and at least one line, to which the measuring means is secured, wherein the line is configured in such a way that that the measurement variables detected by the measuring means can be conducted to the measuring unit.

The invention also pertains to a measurement system for measuring physiological values.

Finally, the invention pertains to the use of the device for establishing contact between a subject and a measuring unit using measurement technology.

It is known that mobile or stationary measuring units can be used to measure properties of the body and body functions of a subject, e.g., a human being or animal. The properties or functions to be measured are often bioimpedances, i.e., body impedances, heart functions, nerve functions, or electrocardiograms. For these measurements, it is necessary to connect the measuring unit to the subject to be measured. Essentially two different possibilities are available for establishing this connection.

First, the measuring unit can comprise contact sites such as gripping or standing surfaces, which, when contacted by the subject, establish the required connection. This realization of the contact between subject and measuring unit is described in, for example, DE 10 2010 023 122 A1. This pertains to a device which establishes the contact between a standing subject and the measuring unit.

The starting point of the invention is a second known device, which realizes the production of contact between the measuring unit and the subject by means of one or more lines, which can be tubes or cables. The lines are usually connected at one end to the measuring unit and to the subject by measuring means such as electrodes. Most body function measurements require several contact points on the subject, frequently on the extremities such as the arms and legs and in many cases on the hands or feet. Exactly one extremity is often assigned to the end of each line. This means that the several measurement sites on the subject must be connected correctly to the measuring means and lines assigned specifically to those sites. Two or more lines, furthermore, are often required for one measurement site on the subject. According to another variant, one line is divided into several smaller lines, each comprising measuring means at its end, all of which are attached to the subject. When this device is used, contact is preferably established while the subject is lying or sitting.

A weak point of the known device is that, when the contacts have been established to the subject—who can be a patient, for example—an extremely unpleasant feeling of being "wired" is produced. Possible consequences could be that the patient breaks off the measurement study or refuses to consider it in the first place.

Another disadvantage is that the correct assignment of the electrodes attached to the ends of the lines to the associated extremities can be realized only on the basis of positioning instructions communicated to the operating personnel by means of visual or tactile clues. There is thus the danger that an electrode can be positioned on the wrong extremity, that is, on the left hand instead of the right hand, on the left foot instead of the right foot, or on a hand instead of a foot—especially when the operators do not pay attention to the instructions or understand them incorrectly.

Another disadvantage of the known device is that the stowing of the lines for transport or storage after the end of the measurement is cumbersome and tedious. There is also the latent danger of damage. A solution to the damage problem upon stowage known from the prior art consists in preventing the lines from snapping or twisting off by providing them with a protective jacket. The jacket, however, does not reliably protect against these forms of damage and causes the lines to become stiff, which makes them more difficult to handle and restricts the freedom of movement of the subject after the measuring means attached to the lines have been connected. The jacketing of the lines also has the effect of increasing the minimum possible coiling radius of the lines, which makes it impossible to stow the lines in a small package. Another disadvantage of this known device is that the lines tend to become knotted, twisted, or tangled. This makes the device even more difficult to manage.

SUMMARY OF THE INVENTION

It is therefore the goal of the invention to create a device of the type described above which offers a general improvement in handling and transport reliability and which lessens the disadvantages described above.

This goal is achieved in that, for the use of measurement technology to establish contact between a subject and a measuring unit, the mat itself accommodates at least certain sections of the lines. The mat is fabricated from a web or curved piece of semi-finished material and has a flat shape. It is preferable to use an elastic, foldable, or rollable material such as plastic, rubber, cardboard, etc. The mat can have a solid surface, or it can be perforated or consist of independent segments or sections or the like. The shape is preferably rectangular or square, but any desired shape is possible.

The advantage achieved by the invention is that, because at least some of the lines are connected to a mat, the extremely unpleasant feeling of being "wired" is lessened or eliminated entirely. The reliability with which the individual measuring means can be assigned to the extremities is improved, because, after the mat has been positioned on or under the subject, the measuring means, such as an electrode, which is the closest is used. Secure stowing in a small package is promoted by the ability of the mat to be rolled or folded up.

The advantageous effects are achieved through the use of a preferably elastic, but in any case at least foldable or rollable mat, which forms at least certain sections of the lines, i.e., lines known from the prior art as means for establishing contact between the subject to be measured and the measuring unit. The electrodes can also be provided in the form of hand electrodes.

According to the invention, arranging the electrodes on the mat makes it unnecessary to adhere the individual electrodes to the skin of the patient. Instead of a large number of cables, each one leading to one of the electrodes, now only a single cable, possibly consisting of several lines, is used to connect the mat to the measuring unit.

To avoid lines for supplying power to the components on the mat, the mat can be equipped with a standard or rechargeable battery. The rechargeable battery can be recharged while the mat is being stored, for example, in a stand provided for the purpose. In addition, the mat can be equipped with control buttons and devices for visualizing the current status, e.g., start, stop, and low battery.

If the mat is configured to fold or roll up suitably, the cables can be secured against falling out during transport and storage.

In a first embodiment, the device according to the invention for measuring physiological values consists of a mat on which at least certain sections of the lines are secured or through which the lines pass. Measuring means are attached to the ends of the lines. The lines comprise an internal section, i.e., a section which extends inside the mat or is secured to the outside surface of the mat, and an external section, that is, a section extending outside the mat.

In the case that a section of the line passes through the interior of the mat, the mat is configured with a cavity in its interior in such a way as to accommodate the internal line section. This can be realized, for example, in that the mat consists of two flexible, plate-like or flat semi-finished products, which are connected to each other along their outside edges.

When a foamable or castable material is used as the starting material for the mat, the internal section of the line can also be embedded directly in the mat material. In a preferred embodiment, the lines can be arranged in such a way that the transition from the internal to the external section of the line occurs in the corner areas of a square or rectangular mat. Another line with an internal and/or external section can be present to connect the device to the measuring unit.

In a second, preferred embodiment, the mat completely replaces the lines used according to the prior art; that is, the lines consist solely of internal sections. If the invention is configured in this way, the measuring means are a direct component of the mat or are secured to the mat. Conventional adhesive electrodes, rest-in-place electrodes, electrode grips, spring-loaded clamping electrodes, or foot-contact electrodes can be used as the measuring means, for example. When electrode grips and foot-contact electrodes are used, the subject to be measured is asked to establish the desired contact between the electrodes and the extremities by touching the electrodes. In the case of electrode grips, these are to be gripped with the hands. By resting the feet on the foot-contact electrodes, the connection with these is produced. When adhesive electrodes are used, the connections are produced by adhering them to the hands and/or feet.

The measuring unit, furthermore, can be arranged externally, i.e., outside and a certain distance away from the mat, or it can be secured to the mat or be an integral component inside the mat. The internal line sections can come together at a point inside the mat, this point being preferably in the center of the mat surface.

The mat can be laid on a sitting or lying subject. The mat can also be used as a substrate for a sitting or lying subject. If the mat according to the invention is configured or used as a substrate under the subject, the extremely unpleasant feeling of being "wired" is reduced even more; the subject is almost completely unaware that he is connected to the lines.

The device according to the invention supports the correct assignment of the measuring means to the individual extremities. Regardless of the shape of the mat, the operator can position the mat relative to the subject in such a way that one of the measuring means will always be closer to one extremity than to any of the others. Thus the assignment of the measuring means is realized simply on the basis of the position of the mat relative to the subject to be measured. Instructions to the operator concerning the correct positioning of the mat relative to the subject to be measured can be provided by orientational or positional information applied to the mat. The mat could also be provided with a picture of the contour of a body, which shows how the mat is to be brought into contact with the subject. If the mat according to the invention in the second preferred embodiment is realized with the use of electrode grips and foot-contact electrodes, the measuring means will be correctly assigned to the hands and feet on the basis of position of the electrode grips and foot-contact electrodes, and the proper left-right assignment will be achieved by orienting the mat so that the front or back side is facing in the appropriate direction.

To support secure stowage in a small package, the mat is configured in such a way that it can be folded or rolled up. When lines with internal and external sections are used, the mat can be folded or rolled up in such a way that the external line sections can be accommodated inside the folded-up or rolled-up mat and are thus prevented from falling out.

The invention is explained in the following with reference to the figures:

DETAILED DESCRIPTION OF THE INVENTION

Figure 1:
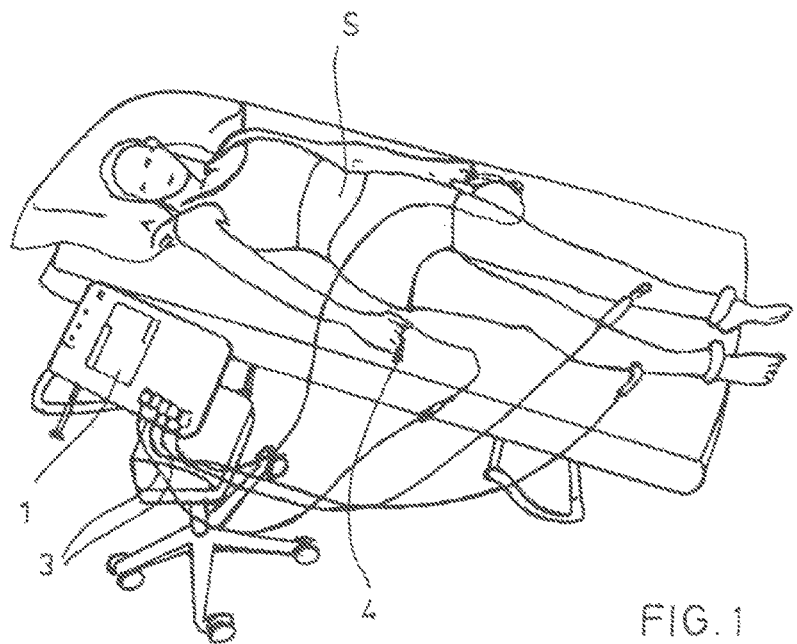
FIG. 1 shows a device for measuring physiological values according to the prior art.

FIG. 1 shows a device for measuring physiological values according to the prior art. The mobile measuring unit 1 is connected to the subject S to be measured by several lines 3 and measuring means 4; that is, the contact between the measuring unit 1 and the subject to be measured is established by lines. The measuring means 4, which are attached to the ends of the lines, are attached to both the hands and the feet of the object. It can be seen that this method of establishing contact between subject S and measuring unit 1 increases the feeling of being "wired"; that the assignment of the measuring means to the individual extremity in question is susceptible to error; and that the lines can become knotted or tangled. It is also known in the prior art that more or fewer lines 3 than the number shown in FIG. 1 are used.

Figure 2:
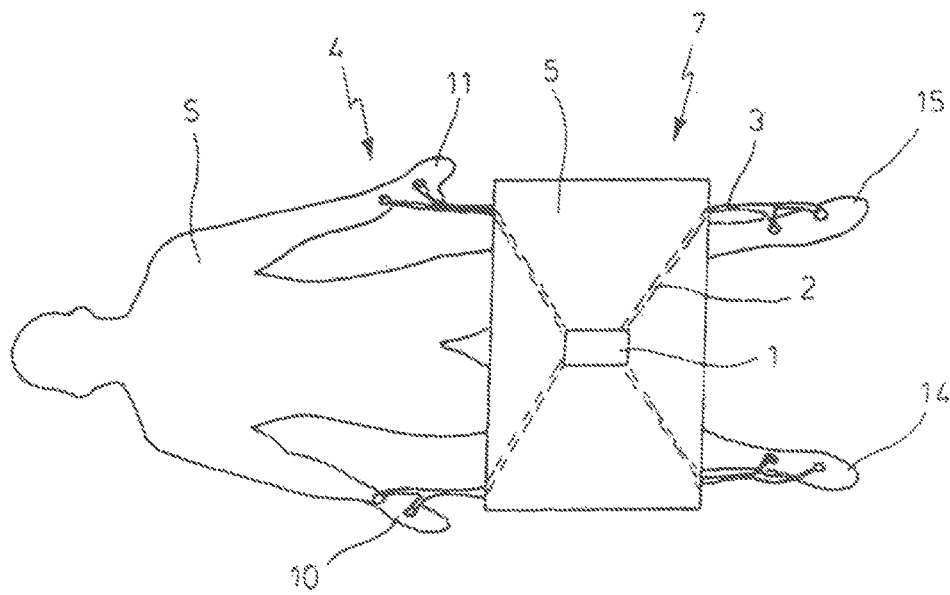
FIG. 2 shows a schematic diagram of a first embodiment of the device for measuring physiological values.

FIG. 2 shows a schematic diagram of a first embodiment of the device 7 according to the invention for establishing contact between measuring means 4 and a measuring unit 7. It consists of a mat 5, which supports or accommodates at least certain sections of the lines extending between the measuring means 4 and the measuring unit 1. The mat 5 comprises lines, to the ends of which the measuring means 4 are attached. The lines comprise an internal section 2; that is, one section of the line extends inside the mat 5 or is attached to the outside surface of the mat 5; and it also comprises an external section 3; that is, another section of the line is located outside the mat 5.

FIG. 2 shows an embodiment according to the invention comprising the measuring unit 1. The measuring unit 1 can be integrated into the mat 5 or mounted on the mat 5. Instead of the integrated structure, the measuring unit 1 can also be arranged outside of the mat 5. The external line sections 3 can be permanently connected to the mat 5 or can be connected in detachable fashion. The attachment can be achieved by means of snap fasteners, for example. The diagram shows the attachment of the external line sections 3 to the corner areas of a rectangular mat 5.

Alternatively, the external line sections 3 can also be attached at any other desired point. It is also possible that the mat 5 could have a shape different from the rectangular one shown. If the measuring unit 1 is an integral component of the mat 5, it can be arranged with itself or at any desired point of the mat 5. The subject S is connected to the measuring unit 1 by the measuring means 4, the associated external line section 3, and the associated internal line section 2.

Figure 3:
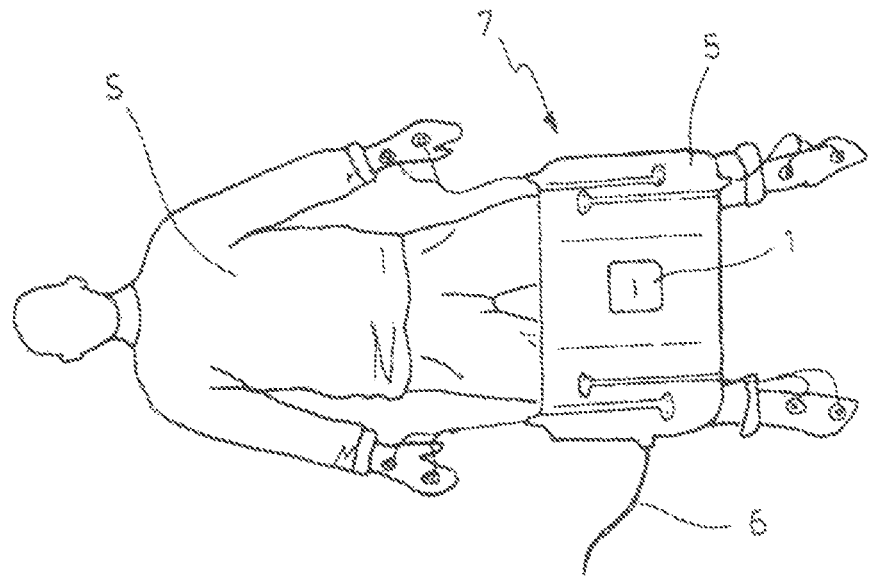
FIG. 3 shows the use of a first embodiment of the device for measuring physiological values.

FIG. 3 shows a drawing of the first embodiment of the device according to the invention for establishing contact between the measuring means 4 and the measuring unit 1. In contrast to the schematic diagram of FIG. 2, the measuring unit 1 is not an integral component of the mat 5 according to the invention; instead, the measuring unit 1 is arranged externally. The measuring unit (not shown) is connected to the mat 5 by a line 6. The rolled-up or folded-up mat 5 can be hung on the housing of the measuring unit 1, for example, which thus supports space-saving transport without the danger that the lines 2, 3 can become tangled, knotted, or twisted. Because the external line sections 3 are attached to the corner areas of the mat 5, the user or operator understands intuitively that the measuring means 4 at the end of the external line section 4 is to be connected to the extremity closest to it.

Figure 4:
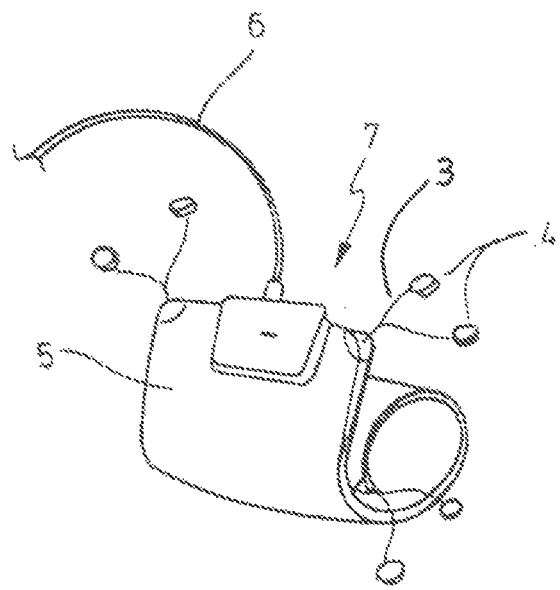
FIG. 4 shows a schematic diagram of the first embodiment of the device for measuring physiological values in the rolled-up state.

FIG. 4 shows a schematic diagram of the first embodiment of the device 7 according to the invention for establishing contact between the measuring means 4 and the measuring unit 1 in a compact state obtained by rolling up the mat. Instead of rolling up the mat 5 to obtain the compact state, the mat 5 could also be folded up. The mat 5 is therefore configured in such a way that it can be brought into a more compact state either by rolling, as shown in FIG. 4, or by folding (not shown).

In the variant with external line sections 3 to the ends of which measuring means 4 are attached, the mat 5 according to the invention is also configured in such a way that the external line sections 3 can be accommodated inside the mat 5 after it has been rolled or folded up and are thus prevented from falling out.

Figure 5:
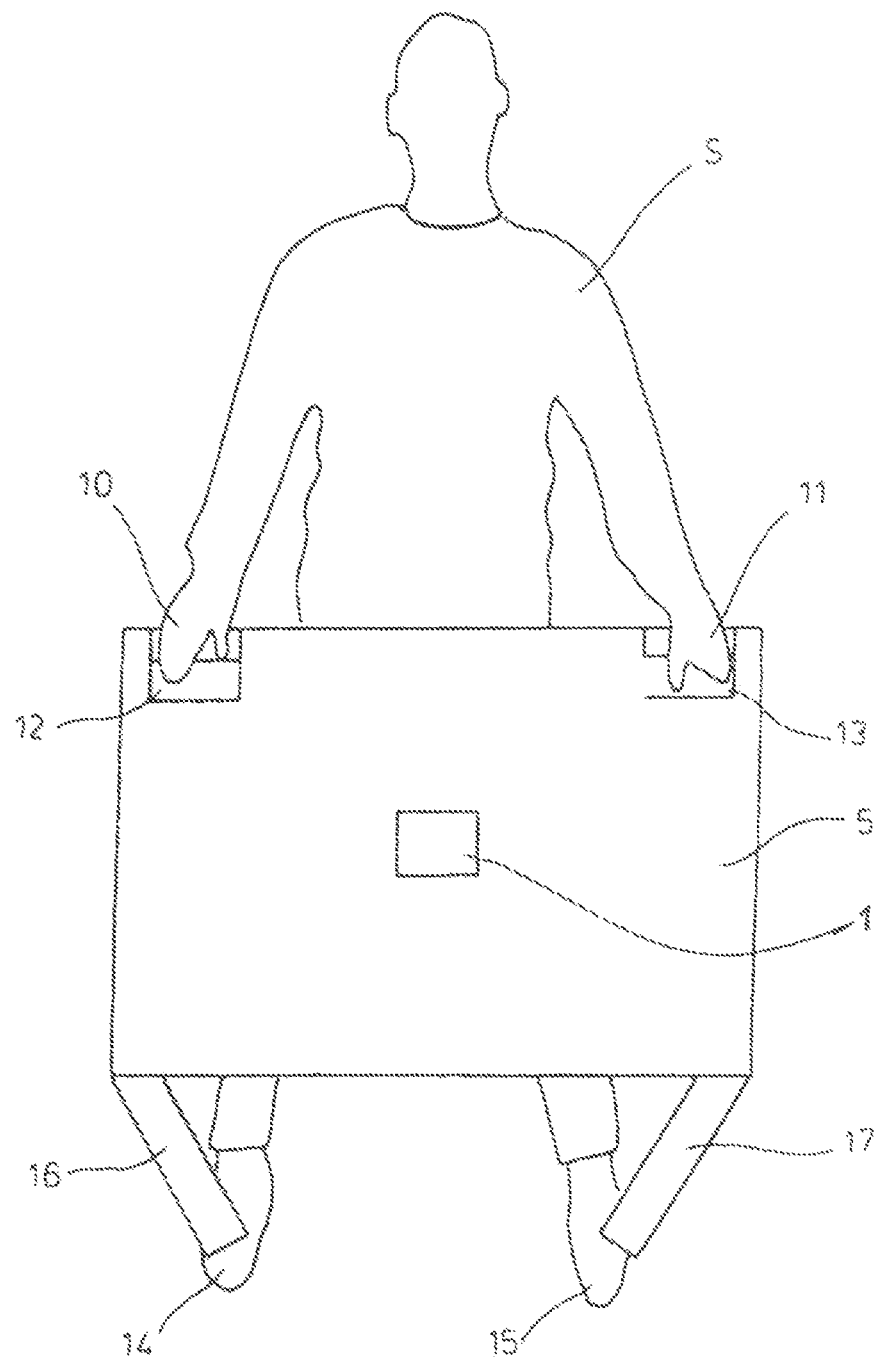
FIG. 5 shows the second embodiment, in which the mat 5 substitutes completely for the lines 3 used according to the prior art, the measuring means being secured directly to the mat.

FIG. 5 shows the subject S, who is using his hands 10, 11 to grip the electrodes 12, 13 arranged in the area of the mat 5. The electrodes 12, 13 in this case constitute parts of the measuring means 4.

To connect the feet 14, 15 of the subject S, extension pieces 16, 17 are arranged on the mat 5. In the area of the extension pieces 16, 17, cables are typically arranged, which connect electrodes positioned in the area of the extension pieces 16, 17 to the measuring unit 1 arranged in the area of the mat 5. The electrodes positioned in the area of the extension pieces 16, 17 can be configured as adhesive electrodes.

The electrodes 12, 13 are preferably arranged adjacent to a first edge of the mat 5. The extension pieces 16, 17 preferably proceed from a second edge opposite the first edge of the mat 5.

According to a variant, the arrangement of the electrodes 12, 13 and extension pieces 16, 17 illustrated in FIG. 5 is reversed. This means that, in the case of the variant, the feet 14, 15 are set down onto special electrodes arranged on the mat 5, and that, via the extension pieces 16, 17, the hands 10, 11 are electrically contacted. In principle, however, it is also conceivable that electrodes could be incorporated into the mat 5 for both the hands 10, 11 and for the feet 14, 15. In an embodiment of this type, it has been found advisable for the mat 5 to be of variable size to accommodate subjects S of different body sizes.

In regard to the structural configuration of the mat 5, an essential design feature consists that the mat 5 guides cables to various body locations of the subject S. More than one cable, therefore, is guided. The mat 5 advisably has a length and a width enabling it to suit the intended application.

According to a preferred application, the measuring unit 1 is configured as a device for detecting and evaluating at least one material composition of the body of the subject in a certain area. In the case of a concrete situation in which the subject S is a human being or patient, a BCA (Body Composition Analyzer) represents a preferred application. By means of a device of this type, what is analyzed in particular is the percentages by weight of the human body accounted for by, for example, fat, muscle mass, and bone mass. The evaluation can also pertain, however, to a many other or additional parameters.

The mat 5 typically comprises at least two corners. Preferably there are at least three corners, and typically there are four corners.

In the case of the exemplary embodiments explained above, it has been specified that in some cases the measuring means 4 can be attached to the mat 5. An attachability of this type comprises any mechanical connection between the measuring means 4 and the mat 5 suitable at least for the implementation of the measuring process. Such means of attachment include in particular permanent adhesive bonds, crimped connections, or merely a temporary connection by way of detachable connecting elements such as hook-and-loop closures or plug-in connectors.

The concept of a "mat" 5 employed many times above comprises, first, soft and/or flexible and/or elastic materials. Alternatively, however, a rigid, board-like or plate-like embodiment can also be realized. In addition, a configuration consisting of several rigid segments connected to each other is also conceivable, which can be folded up and positioned over or under the subject. An embodiment of this type can be realized in a manner similar to that of a tank tread.

As an alternative to the use of a line 6 to transmit an electrical signal, the use of wireless connections is also possible, such as the use of a radio link. According to a special embodiment, the mat 5 is provided with a display device. The display device can, for example, visualize the current operating status. It is also possible that the display could visualize malfunctions or operating errors. Measuring unit operating instructions and/or a measuring result display (GUI) is also possible. With respect to operating reliability, indications of functional or operating errors can also be conveyed acoustically.

A characterization or selection of the positioning of the device 7 can be done automatically, for example, by a position-detection system. Alternatively, a corresponding characterization or selection can also be achieved manually by means of pushbuttons on the mat 5 or on the measuring unit 1.

The invention claimed is:

1. A device for establishing contact between a human being and a measuring unit using measurement technology, comprising: at least one measuring device attachable to each hand and each foot of the human being; at least four lines to which the measuring device is attached, wherein the lines are configured to conduct measurement variables detected by the measuring device to the measuring unit for detecting and evaluating bioimpedance data; and, a flexible mat connected to the lines so that at least part of each of the lines forms an internal line section internal to the mat, wherein the measuring device includes electrodes for carrying out a bioimpedance measurement, the electrodes including at least one electrode for each hand of the human being and at least one electrode for each foot of the human being, wherein the electrodes are incorporated in the mat, wherein the electrodes are arranged in the mat so that the hands and the feet of the human being are contacted by the corresponding electrodes when the mat is placed on the human being, each of the four lines being connected to a respective one of the electrodes.

2. The device according to claim 1, wherein the internal line section is an integral component of the mat.

3. The device according to claim 1, wherein the at least one measuring device is arranged in a corner area section of the mat.

4. The device according to claim 1, wherein the mat is rollable or foldable into a compact state.

5. The device according to claim 1, wherein the mat has an integrated power supply.

6. The device according to claim 5, wherein the power supply is a battery.

7. The device according to claim 1, wherein the measuring unit is an integral component of the mat and is connected to the line sections.

8. The device according to claim 1, wherein the measuring unit is securable to a surface of the mat and is connected to the line sections.

9. The device according to claim 1, wherein the mat has connection means for connecting the measuring unit located a distance away from the mat.

10. The device according to claim 1, wherein the electrodes are adhesive electrodes.

* * * * *